US00PP37040P2

(12) United States Plant Patent
de Vos

(10) Patent No.: US PP37,040 P2
(45) Date of Patent: Oct. 21, 2025

(54) ***HYDRANGEA* PLANT NAMED 'HORE9103'**

(50) Latin Name: *Hydrangea macrophylla*
Varietal Denomination: HORE9103

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 19/030,080

(22) Filed: Jan. 17, 2025

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

*Primary Examiner* — Susan McCormick Ewoldt
(74) *Attorney, Agent, or Firm* — C. Anne Whealy

(57) ABSTRACT

A new and distinct cultivar of *Hydrangea* plant named 'HORE9103', characterized by its relatively compact, upright to broadly spreading plant habit; relatively moderately vigorous growth habit; freely branching habit; strong and sturdy stems; freely flowering habit; panicles with double-type sterile flowers that are light purple in color; and good postproduction longevity.

2 Drawing Sheets

Figure 1:
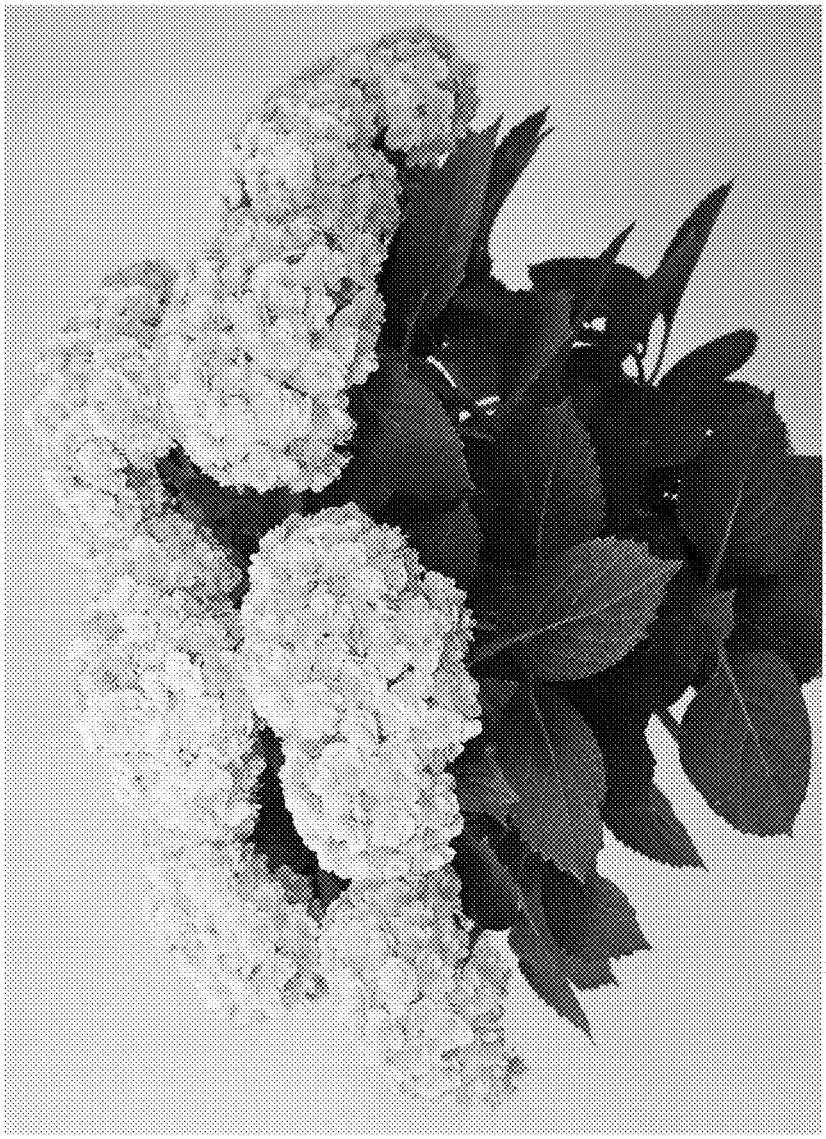

Botanical designation: *Hydrangea macrophylla.*
Cultivar denomination: 'HORE9103'.

CROSS-REFERENCED TO CLOSELY-RELATED APPLICATIONS

A United Kingdom Plant Breeder's Rights application for this plant was filed by the Applicant/Assignee of the instant application, Kwekerij Lendert de Vos of Reeuwijk, The Netherlands on Aug. 20, 2024, application number 23/884, and published on Sep. 1, 2024. Foreign priority is not claimed to this United Kingdom Plant Breeder's Rights application.

A European Community Plant Breeder's Rights application for this plant was filed by the Applicant/Assignee of the instant application, Kwekerij Lendert de Vos of Reeuwijk, The Netherlands on Sep. 24, 2024, application number 2024/2227, and published on Dec. 15, 2024. Foreign priority is not claimed to this European Plant Breeder's Rights application.

BACKGROUND OF THE INVENTION

The present invention relates to a new and distinct cultivar of *Hydrangea* plant, botanically known as *Hydrangea macrophylla*, commercially referred to as a Bigleaf *Hydrangea* and hereinafter referred to by the name 'HORE9103'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from a cross-pollination in August 2017 of a proprietary selection of *Hydrangea macrophylla* identified as code number 16-20139-02, not patented, as the female, or seed, parent with a proprietary of *Hydrangea macrophylla* identified as code number 16-20143-03, not patented, as the male, or pollen, parent. The new *Hydrangea* plant was discovered and selected as a single flowering plant from within the progeny of the stated cross-pollination in a controlled greenhouse environment in Reeuwijk, The Netherlands in August 2019.

Asexual reproduction of the new *Hydrangea* plant by terminal vegetative cuttings since August 2019 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HORE9103'. These characteristics in combination distinguish 'HORE9103' as a new and distinct *Hydrangea* plant:

1. Relatively compact, upright to broadly spreading plant habit.
2. Relatively moderately vigorous growth habit.
3. Freely branching habit.
4. Strong and sturdy stems.
5. Freely flowering habit.
6. Panicles with double-type sterile flowers that are light purple in color.
7. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* have double-type sterile flowers whereas plants of the female parent selection have single-type sterile flowers.
2. Flowers of plants of the new *Hydrangea* are sterile whereas flowers of plants of the female parent selection are fertile.

Plants of the new *Hydrangea* can be compared to plants of the male parent selection. Plants of the new *Hydrangea* differ primarily from plants of the male parent selection in the following characteristics:

1. Plants of the new *Hydrangea* are more compact than plants of the male parent selection.
2. Plants of the new *Hydrangea* have double-type sterile flowers whereas plants of the male parent selection have single-type sterile flowers.
3. Flowers of plants of the new *Hydrangea* are sterile whereas flowers of plants of the male parent selection are fertile.

Plants of the new *Hydrangea* can be compared to plants of *Hydrangea macrophylla* 'Youmefive', not patented. In side-by-side comparisons, plants of the new *Hydrangea* differ primarily from plants of 'Youmefive' in the following characteristics:

1. Plants of the new *Hydrangea* are more freely branching than plants of 'Youmefive'.
2. Inflorescences of plants of the new *Hydrangea* are more uniformly rounded than inflorescences of plants of 'Youmefive'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HORE9103' grown in a container.

Figure 2:
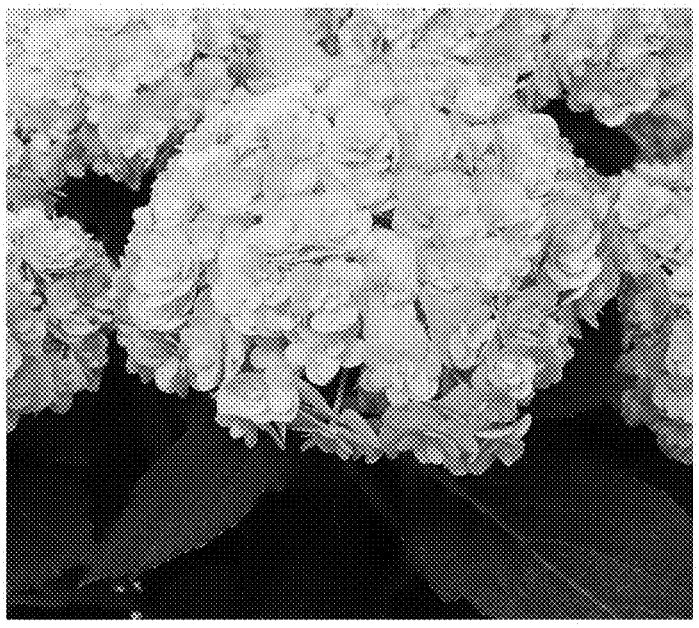

The photograph at the top of the second sheet (FIG. 2) is a close-up view of typical inflorescences of 'HORE9103'.

Figure 3:
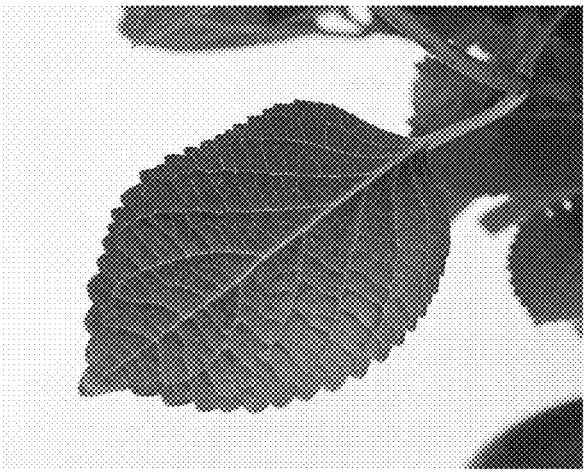

The photograph at the bottom of the second sheet (FIG. 3) is a close-up view of typical leaves of 'HORE9103'.

DETAILED BOTANICAL DESCRIPTION

Plants used in the aforementioned photographs and in the following description were grown during the summer in 14-cm containers in a glass-covered greenhouse in Reeuwijk, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were pinched one time and were 18 months old when the photographs and description were taken. In the following description, color references are made to The Royal Horticultural Society Colour Chart, Sixth Edition, except where general terms of ordinary dictionary significance are used. The new *Hydrangea* plant is not typically treated with aluminum sulfate to "blue" the flower color.

Botanical description: *Hydrangea macrophylla* 'HORE9103'.

Parentage:

*Female, or seed, patent*.—Proprietary selection of *Hydrangea macrophylla* identified as code number 16-20139-02, not patented.

*Male, or pollen, patent*.—Proprietary selection of *Hydrangea macrophylla* identified as code number 16-20143-03, not patented.

Propagation:

*Type cutting*.—By vegetative terminal cuttings.

*Time to initiate roots, summer*.—About 16 days at temperatures ranging from 20° C. to 30° C.

*Time to produce a rooted young plant, summer*.—About four months at temperatures ranging from 20° C. to 30° C.

*Root description*.—Medium in thickness; fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Relatively compact; upright to broadly outwardly spreading and mounding plant habit; overall shape, flattened globular; strong and sturdy stems; relatively moderately vigorous growth habit and moderate growth rate; about six months from propagation are required to produce small finished plants.

*Plant height*.—About 35 cm.

*Plant diameter or area of spread*.—About 58.8 cm.

Lateral branch description:

*Branching habit*.—Freely branching habit with about 15 lateral branches developing per plant; pinching is not required, but will enhance lateral branch development.

*Length*.—About 20.1 cm.

*Diameter*.—About 5 mm.

*Internode length*.—About 3.8 cm.

*Strength*.—Strong, sturdy.

*Aspect*.—Erect to about 60° from vertical.

*Texture*.—Smooth, glabrous; becoming woody with subsequent development.

*Color, developing*.—Close to 144A.

*Color, fully developed*.—Close to 144A to 144B; at the nodes, slightly tinged with close to 183D; when woody, close to 199B and N199C.

*Lenticels*.—Density: Medium density. Length: About 0.8 mm. Diameter: About 0.5 mm. Color: Close to N186C.

Leaf description:

*Arrangement*.—Opposite, simple.

*Length*.—About 9.1 cm.

*Width*.—About 6.7 cm.

*Shape*.—Broadly ovate.

*Apex*.—Apiculate.

*Base*.—Obtuse to short acute.

*Margin*.—Coarsely dentate-serrate.

*Texture and luster, upper surface*.—Smooth, glabrous; somewhat glossy.

*Texture and luster, lower surface*.—Smooth, glabrous; slightly rugose; slightly glossy.

*Venation pattern*.—Pinnate.

*Color*.—Developing leaves, upper surface: Close to 137A. Developing leaves, lower surface: Close to 146A. Fully developed leaves, upper surface: Close to a blend of 147A and N189A; venation, close to 146D. Fully developed leaves, lower surface: Close to 147B; venation, close to 146D.

*Petioles*.—Length: About 2.3 cm. Diameter: About 3 mm. Texture and luster, upper and lower surfaces: Smooth, glabrous; slightly glossy. Color, upper and lower surfaces: Close to 144A.

Flower description:

*Flower type and habit*.—Rotate double-type sterile flowers arranged on terminal hemispherical panicles; panicles flattened globular in overall shape; sterile flowers face upright to outwardly; to date, fertile flower development has not been observed on plants of the new *Hydrangea*.

*Fragrance*.—None detected.

*Natural flowering season*.—Plants flower continuously for about three months; in garden in The Netherlands, plants flower from late spring into the late summer.

*Flower longevity*.—Good postproduction longevity; sterile flowers maintain good substance for about six weeks on the plant, sterile flowers persistent.

*Quantity of flowers*.—Freely flowering habit; about 400 sterile flowers per panicle.

*Panicle height*.—About 8.1 cm.

*Panicle diameter*.—About 15.2 cm.

*Panicle peduncles*.—Length: About 9.6 cm. Diameter: About 4.5 mm. Strength: Strong. Aspect: Primary peduncles, mostly erect; lateral peduncles, about 30° from primary peduncle axis. Texture and luster: Moderately to densely pubescent; matte. Color: Close to 144B; at the nodes, tinged with close to 177A and 177B. Lenticels: Density: Sparse. Length: About 0.8 mm. Diameter: About 0.5 mm. Color: Close to 200C.

*Sterile flower buds*.—Length: About 7 mm. Diameter: About 1.2 cm. Shape: Cup-shaped. Color: Close to 75C.

*Sterile flower diameter*.—About 2.2 cm.

*Sterile flower depth* (*height*).—About 9 mm.

*Petals, sterile flowers*.—To date, petal development has not been observed on sterile flowers of plants of the new *Hydrangea*.

*Sepals, sterile flowers*.—Quantity and arrangement: About 18 in multiple whorls. Length, largest sepals: About 1.1 cm. Width, largest sepals: About 9 mm. Shape: Broadly ovate; mostly flat to slightly concave. Apex: Obtuse. Base: Broadly attenuate. Margin: Entire. Texture and luster, upper and lower surfaces: Smooth, glabrous; matte. Color: When opening, upper surface: Close to 75B. When opening, lower surface: Close to a blend of 75B and 75C. Fully opened, upper surface: Close to 75C; towards the apex, close to 75D; with subsequent development, color becoming closer to 145C. Fully opened, lower surface: Close to 75C; towards the apex, close to 75D; with subsequent development, color becoming closer to 145D.

*Pedicels, sterile flowers*.—Length: About 1.4 cm. Diameter: About 1 mm. Strength: Moderately strong. Aspect: About 35° from main peduncle axis Texture and luster: Moderately to densely pubescent; matte. Color: Close to 75C; proximal end, tinged with close to 145D.

*Reproductive organs, sterile flowers*.—Stamens: To date, stamen development has not been observed on plants of the new *Hydrangea*. Pistils: Pistil quantity per flower: Typically six. Pistil length: About 1 mm. Stigma shape: Club-shaped. Stigma color: Close to NN155D. Style length: About 0.75 mm. Style color: Close to NN155A. Ovary color: Close to a blend of 75D and NN155A.

*Fruits and seeds*.—To date, fruit and seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HORE9103' as herein illustrated and described.

* * * * *